(12) United States Patent
Steward et al.

(10) Patent No.: US 7,671,177 B2
(45) Date of Patent: Mar. 2, 2010

(54) LEUCINE-BASED MOTIF AND CLOSTRIDIAL NEUROTOXINS

(75) Inventors: Lance E. Steward, Irvine, CA (US);
Todd M. Herrington, Irvine, CA (US);
Kei Roger Aoki, Coto De Caza, CA (US)

(73) Assignee: Allergan, Inc., Irvine, CA (US)

( * ) Notice: Subject to any disclaimer, the term of this patent is extended or adjusted under 35 U.S.C. 154(b) by 106 days.

(21) Appl. No.: 12/057,642

(22) Filed: Mar. 28, 2008

(65) Prior Publication Data

US 2008/0177042 A1    Jul. 24, 2008

Related U.S. Application Data

(62) Division of application No. 11/039,268, filed on Jan. 19, 2005, now Pat. No. 7,393,925, which is a division of application No. 09/620,840, filed on Jul. 21, 2000, now Pat. No. 6,903,187.

(51) Int. Cl.
*C07K 14/33* (2006.01)

(52) U.S. Cl. .................... 530/350; 530/825

(58) Field of Classification Search ............ None
See application file for complete search history.

(56) References Cited

U.S. PATENT DOCUMENTS

| | | | |
|---|---|---|---|
| 4,932,936 | A | 6/1990 | Dykstra et al. |
| 5,053,005 | A | 10/1991 | Borodic |
| 5,437,291 | A | 8/1995 | Pasricha et al. |
| 5,714,468 | A | 2/1998 | Binder |
| 5,721,215 | A | 2/1998 | Aoki et al. |
| 5,766,605 | A | 6/1998 | Sanders et al. |
| 5,939,070 | A | 8/1999 | Johnson et al. |
| 5,989,545 | A | 11/1999 | Foster et al. |
| 6,113,915 | A | 9/2000 | Aoki et al. |
| 6,139,845 | A | 10/2000 | Donovan |
| 6,143,306 | A | 11/2000 | Donovan |
| 6,265,379 | B1 | 7/2001 | Donovan |
| 6,306,403 | B1 | 10/2001 | Donovan |
| 6,306,423 | B1 | 10/2001 | Donovan |
| 6,312,708 | B1 | 11/2001 | Donovan |
| 6,328,977 | B1 | 12/2001 | Donovan |
| 6,358,513 | B1 | 3/2002 | Voet et al. |
| 6,458,365 | B1 | 10/2002 | Aoki et al. |
| 6,464,986 | B1 | 10/2002 | Aoki et al. |
| 6,903,187 | B1 | 6/2005 | Steward et al. |
| 7,393,925 | B2 | 7/2008 | Steward et al. |
| 2002/0127247 | A1 | 9/2002 | Steward et al. |

FOREIGN PATENT DOCUMENTS

| | | |
|---|---|---|
| WO | WO 94/15629 | 7/1994 |
| WO | WO 96/39166 | 12/1996 |
| WO | WO 97/32599 | 9/1997 |
| WO | WO 00/05252 | 2/2000 |

OTHER PUBLICATIONS

Binz et al, J. Biol Chem 265:9153-9156 (1990).
Shin et al, "Phosphorylation-Dependent Down-Modulation . . . " J. Biol Chem 266: 10658-10665 (1991).
Raciborska et al, "Retention of Cleaved Synaptosome-Associated . . . " Can. J. Physiol 77:679-688 (1999).
Fernandez-Salas, E., et al., *Plasma membrane localization signals in the light chain of Botulinum neurotoxin*, Proceedings of the National Academy of Sciences of the United States of America, Mar. 2, 2004, vol. 101, No. 9, pp. 3208-3213.
Erdal et al, Arch. Pharmacol 351: 67-78 (1995).
Ragona et al, "Management of Parotid Sialocele . . . ", The Laryngoscope 109:1344-1346 (1999).
Naumann et al, "Botulinum Toxin Type A in the Treatment . . . ", Eur. J. Neurol, 6: S111-S115 (1999).
Keller et al, "Persistence of Botulinum Neurotoxin", FEBS Lett. 456: 137-142 (1999).
Dietrich et al, "Regulation and Function of the CD3yDxxxLL Motif . . . ", J. Cell. Biol 138: 271-281 (1997).
Geisler et al, "Leucine-Based Receptor Sorting Motifs . . . ", J. Biol. Chem. 273:21316-21323 (1998).
Tan et al, A Leucine-Based Motif Mediates the Endocytosis . . . , J. Biol. Chem. 273: 17351-17360 (1998).
Liu et al, "Membrane Trafficking of Neurotransmitter . . . ", Trends Cell. Biol. 9: 356-363 (1999).
Cai et al, "A Correlation Between Differential Structural Features and the Degree of Endopeptidase", Biochemistry 40 (15): 4693-4702 (2001).
Minton, "Molecular genetics of Clostridial Neurotoxins", Montecucco C. (Ed.) Clostridial Neurotoxins in the molecular pathogenesis of tetanus and botulism, 161-194 (1995).
Fernandez-Salas, E., et al., "Plasma membrane signals in the light chain of Botulinum neurotoxin", slide presentation at USAMRDD, Jan. 2004.

(Continued)

*Primary Examiner*—Robert C Hayes
(74) *Attorney, Agent, or Firm*—Dean G. Stathakis; Joel B. German; Allergan, Inc.

(57) ABSTRACT

Modified neurotoxin comprising neurotoxin including structural modification, wherein the structural modification alters the biological persistence, preferably the biological half-life, of the modified neurotoxin relative to an identical neurotoxin without the structural modification. The structural modification includes addition or deletion of a leucine-based motif or parts thereof. In one embodiment, methods of making the modified neurotoxin include using recombinant techniques. In another embodiment, methods of using the modified neurotoxin to treat biological disorders include treating autonomic disorders, neuromuscular disorders or pains.

4 Claims, No Drawings

OTHER PUBLICATIONS

Fernandez-Salas, E., et al., "Is the light chain subcellular localization an important factor in Botulinum toxin duration of action?", Movement Disorders (2004) 19: S23-S34.

Schantz et al, "Properties and use of Botulinum toxin and other microbial neurotoxins in medicine", Microbiological Reviews, vol. 56, No. 1, 80-89 (Mar. 1992).

Radinger In , "Peptide Hormones", ed. J.A. Parsons, "Characterizations of the amino acids as components of a peptide hormone sequence", University Part Press, Baltimore, pp. 1-7, (1976).

Zhou et al, "Expression and purification of the light chain of botulinum neurotoxin A: A single mutation abolishes its cleavage of SNAP-25 and neurotoxicity after reconstruction with the heavy chain", Biochemistry, vol. 34, No. 46, pp. 15175-15181, 1995.

```
                         SEQUENCE LISTING

<160> NUMBER OF SEQ ID NOS: 18

<210> SEQ ID NO 1
<211> LENGTH: 7
<212> TYPE: PRT
<213> ORGANISM: Artificial Sequence
<220> FEATURE:
<223> OTHER INFORMATION: Consensus sequence for Leucine-based motif.
<221> NAME/KEY: VARIANT
<222> LOCATION: (1)...(1)
<223> OTHER INFORMATION: Xaa is any amino acid.
<221> NAME/KEY: VARIANT
<222> LOCATION: (3)...(5)
<223> OTHER INFORMATION: Xaa is any amino acid.

<400> SEQUENCE: 1

Xaa Asp Xaa Xaa Xaa Leu Leu
1               5

<210> SEQ ID NO 2
<211> LENGTH: 7
<212> TYPE: PRT
<213> ORGANISM: Artificial Sequence
<220> FEATURE:
<223> OTHER INFORMATION: Consensus sequence for Leucine-based motif.
<221> NAME/KEY: VARIANT
<222> LOCATION: (1)...(1)
<223> OTHER INFORMATION: Xaa is any amino acid.
<221> NAME/KEY: VARIANT
<222> LOCATION: (3)...(5)
<223> OTHER INFORMATION: Xaa is any amino acid.

<400> SEQUENCE: 2

Xaa Glu Xaa Xaa Xaa Leu Leu
1               5

<210> SEQ ID NO 3
<211> LENGTH: 7
<212> TYPE: PRT
<213> ORGANISM: Artificial Sequence
<220> FEATURE:
<223> OTHER INFORMATION: Consensus sequence for Leucine-based motif.
<221> NAME/KEY: VARIANT
<222> LOCATION: (1)...(1)
<223> OTHER INFORMATION: Xaa is any amino acid.
<221> NAME/KEY: VARIANT
<222> LOCATION: (3)...(5)
<223> OTHER INFORMATION: Xaa is any amino acid.

<400> SEQUENCE: 3

Xaa Asp Xaa Xaa Xaa Leu Ile
1               5
```

```
<210> SEQ ID NO 4
<211> LENGTH: 7
<212> TYPE: PRT
<213> ORGANISM: Artificial Sequence
<220> FEATURE:
<223> OTHER INFORMATION: Consensus sequence for Leucine-based motif.
<221> NAME/KEY: VARIANT
<222> LOCATION: (1)...(1)
<223> OTHER INFORMATION: Xaa is any amino acid.
<221> NAME/KEY: VARIANT
<222> LOCATION: (3)...(5)
<223> OTHER INFORMATION: Xaa is any amino acid.

<400> SEQUENCE: 4

Xaa Asp Xaa Xaa Xaa Leu Met
1               5

<210> SEQ ID NO 5
<211> LENGTH: 7
<212> TYPE: PRT
<213> ORGANISM: Artificial Sequence
<220> FEATURE:
<223> OTHER INFORMATION: Consensus sequence for Leucine-based motif.
<221> NAME/KEY: VARIANT
<222> LOCATION: (1)...(1)
<223> OTHER INFORMATION: Xaa is any amino acid.
<221> NAME/KEY: VARIANT
<222> LOCATION: (3)...(5)
<223> OTHER INFORMATION: Xaa is any amino acid.

<400> SEQUENCE: 5

Xaa Glu Xaa Xaa Xaa Leu Ile
1               5

<210> SEQ ID NO 6
<211> LENGTH: 7
<212> TYPE: PRT
<213> ORGANISM: Artificial Sequence
<220> FEATURE:
<223> OTHER INFORMATION: Consensus sequence for Leucine-based motif.
<221> NAME/KEY: VARIANT
<222> LOCATION: (1)...(1)
<223> OTHER INFORMATION: Xaa is any amino acid.
<221> NAME/KEY: VARIANT
<222> LOCATION: (3)...(5)
<223> OTHER INFORMATION: Xaa is any amino acid.

<400> SEQUENCE: 6

Xaa Glu Xaa Xaa Xaa Leu Met
1               5

<210> SEQ ID NO 7
<211> LENGTH: 7
<212> TYPE: PRT
<213> ORGANISM: Clostridial botulinum serotype A

<400> SEQUENCE: 7

Phe Glu Phe Tyr Lys Leu Leu
1               5

<210> SEQ ID NO 8
<211> LENGTH: 7
<212> TYPE: PRT
<213> ORGANISM: Rattus norvegicus

<400> SEQUENCE: 8

Glu Glu Lys Arg Ala Ile Leu
1               5
```

<210> SEQ ID NO 9
<211> LENGTH: 7
<212> TYPE: PRT
<213> ORGANISM: Rattus norvegicus

<400> SEQUENCE: 9

Glu Glu Lys Met Ala Ile Leu
1               5

<210> SEQ ID NO 10
<211> LENGTH: 7
<212> TYPE: PRT
<213> ORGANISM: Rattus norvegicus

<400> SEQUENCE: 10

Ser Glu Arg Asp Val Leu Leu
1               5

<210> SEQ ID NO 11
<211> LENGTH: 7
<212> TYPE: PRT
<213> ORGANISM: Rattus norvegicus

<400> SEQUENCE: 11

Val Asp Thr Gln Val Leu Leu
1               5

<210> SEQ ID NO 12
<211> LENGTH: 7
<212> TYPE: PRT
<213> ORGANISM: Mus musculus

<400> SEQUENCE: 12

Ala Glu Val Gln Ala Leu Leu
1               5

<210> SEQ ID NO 13
<211> LENGTH: 7
<212> TYPE: PRT
<213> ORGANISM: Xenopus laevis

<400> SEQUENCE: 13

Ser Asp Lys Gln Asn Leu Leu
1               5

<210> SEQ ID NO 14
<211> LENGTH: 7
<212> TYPE: PRT
<213> ORGANISM: Gallus gallus

<400> SEQUENCE: 14

Ser Asp Arg Gln Asn Leu Ile
1               5

<210> SEQ ID NO 15
<211> LENGTH: 7
<212> TYPE: PRT
<213> ORGANISM: Sheep

<400> SEQUENCE: 15

Ala Asp Thr Gln Val Leu Met
1               5

```
<210> SEQ ID NO 16
<211> LENGTH: 7
<212> TYPE: PRT
<213> ORGANISM: Homo sapiens

<400> SEQUENCE: 16

Ser Asp Lys Asn Thr Leu Leu
1               5

<210> SEQ ID NO 17
<211> LENGTH: 7
<212> TYPE: PRT
<213> ORGANISM: Homo sapiens

<400> SEQUENCE: 17

Ser Gln Ile Lys Arg Leu Leu
1               5

<210> SEQ ID NO 18
<211> LENGTH: 7
<212> TYPE: PRT
<213> ORGANISM: Homo sapiens

<400> SEQUENCE: 18

Ala Asp Thr Gln Ala Leu Leu
1               5
```

LEUCINE-BASED MOTIF AND CLOSTRIDIAL NEUROTOXINS

This application is a divisional and claims priority pursuant to 35 U.S.C. §120 to U.S. patent application Ser. No. 11/039,268, filed Jan. 19, 2005, now U.S. Pat. No. 7,393,925, which is a divisional application that claims priority pursuant to 35 U.S.C. §120 to U.S. patent application Ser. No. 09/620,840, filed Jul. 21, 2000, now U.S. Pat. No. 6,903,187, each of which is hereby incorporated by reference in its entirety.

BACKGROUND

The present invention relates to modified neurotoxins, particularly modified Clostridial neurotoxins, and use thereof to treat various disorders, including neuromuscular disorders, autonomic nervous system disorders and pain.

The clinical use of *botulinum* toxin serotype A (herein after "BoNT/A"), a serotype of Clostridial neurotoxin, represents one of the most dramatic role reversals in modern medicine: a potent biologic toxin transformed into a therapeutic agent. BoNT/A has become a versatile tool in the treatment of a wide variety of disorders and conditions characterized by muscle hyperactivity, autonomic nervous system hyperactivity and/or pain.

Botulinum toxin

The anaerobic, gram positive bacterium *Clostridium botulinum* produces a potent polypeptide neurotoxin, *botulinum* toxin, which causes a neuroparalytic illness in humans and animals referred to as botulism. The spores of *Clostridium botulinum* are found in soil and can grow in improperly sterilized and sealed food containers of home based canneries, which are the cause of many of the cases of botulism. The effects of botulism typically appear 18 to 36 hours after eating the foodstuffs infected with a *Clostridium botulinum* culture or spores. The *botulinum* toxin can apparently pass unattenuated through the lining of the gut and attack peripheral motor neurons. Symptoms of *botulinum* toxin intoxication can progress from difficulty walking, swallowing, and speaking to paralysis of the respiratory muscles and death.

BoNT/A is the most lethal natural biological agent known to man. About 50 picograms of *botulinum* toxin (purified neurotoxin complex) serotype A is a $LD_{50}$ in mice. One unit (U) of *botulinum* toxin is defined as the $LD_{50}$ upon intraperitoneal injection into female Swiss Webster mice weighing 18-20 grams each. Seven immunologically distinct *botulinum* neurotoxins have been characterized, these being respectively *botulinum* neurotoxin serotypes A, B, $C_1$, D, E, F and G each of which is distinguished by neutralization with serotype-specific antibodies. The different serotypes of *botulinum* toxin vary in the animal species that they affect and in the severity and duration of the paralysis they evoke. For example, it has been determined that BoNt/A is 500 times more potent, as measured by the rate of paralysis produced in the rat, than is *botulinum* toxin serotype B (BoNT/B). Additionally, BoNt/B has been determined to be non-toxic in primates at a dose of 480 U/kg which is about 12 times the primate $LD_{50}$ for BoNt/A. *Botulinum* toxin apparently binds with high affinity to cholinergic motor neurons, is translocated into the neuron and blocks the release of acetylcholine.

*Botulinum* toxins have been used in clinical settings for the treatment of neuromuscular disorders characterized by hyperactive skeletal muscles. BoNt/A has been approved by the U.S. Food and Drug Administration for the treatment of blepharospasm, strabismus and hemifacial spasm. Non-serotype A *botulinum* toxin serotypes apparently have a lower potency and/or a shorter duration of activity as compared to BoNt/A. Clinical effects of peripheral intramuscular BoNt/A are usually seen within one week of injection. The typical duration of symptomatic relief from a single intramuscular injection of BoNt/A averages about three months.

Although all the *botulinum* toxins serotypes apparently inhibit release of the neurotransmitter acetylcholine at the neuromuscular junction, they do so by affecting different neurosecretory proteins and/or cleaving these proteins at different sites. For example, *botulinum* serotypes A and E both cleave the 25 kiloDalton (kD) synaptosomal associated protein (SNAP-25), but they target different amino acid sequences within this protein. BoNT/B, D, F and G act on vesicle-associated protein (VAMP, also called synaptobrevin), with each serotype cleaving the protein at a different site. Finally, *botulinum* toxin serotype $C_1$ (BoNT/$C_1$) has been shown to cleave both syntaxin and SNAP-25. These differences in mechanism of action may affect the relative potency and/or duration of action of the various *botulinum* toxin serotypes.

Regardless of serotype, the molecular mechanism of toxin intoxication appears to be similar and to involve at least three steps or stages. In the first step of the process, the toxin binds to the presynaptic membrane of the target neuron through a specific interaction between the H chain and a cell surface receptor; the receptor is thought to be different for each serotype of *botulinum* toxin and for tetanus toxin. The carboxyl end segment of the H chain, $H_c$, appears to be important for targeting of the toxin to the cell surface.

In the second step, the toxin crosses the plasma membrane of the poisoned cell. The toxin is first engulfed by the cell through receptor-mediated endocytosis, and an endosome containing the toxin is formed. The toxin then escapes the endosome into the cytoplasm of the cell. This last step is thought to be mediated by the amino end segment of the H chain, $H_N$, which triggers a conformational change of the toxin in response to a pH of about 5.5 or lower. Endosomes are known to possess a proton pump which decreases intra endosomal pH. The conformational shift exposes hydrophobic residues in the toxin, which permits the toxin to embed itself in the endosomal membrane. The toxin then translocates through the endosomal membrane into the cytosol.

The last step of the mechanism of *botulinum* toxin activity appears to involve reduction of the disulfide bond joining the H and L chain. The entire toxic activity of *botulinum* and tetanus toxins is contained in the L chain of the holotoxin; the L chain is a zinc (Zn++) endopeptidase which selectively cleaves proteins essential for recognition and docking of neurotransmitter-containing vesicles with the cytoplasmic surface of the plasma membrane, and fusion of the vesicles with the plasma membrane. Tetanus neurotoxin, *botulinum* toxin/B/D,/F, and/G cause degradation of synaptobrevin (also called vesicle-associated membrane protein (VAMP)), a synaptosomal membrane protein. Most of the VAMP present at the cytosolic surface of the synaptic vesicle is removed as a result of any one of these cleavage events. Each toxin specifically cleaves a different bond.

The molecular weight of the *botulinum* toxin protein molecule, for all seven of the known *botulinum* toxin serotypes, is about 150 kD. Interestingly, the *botulinum* toxins are released by Clostridial bacterium as complexes comprising the 150 kD *botulinum* toxin protein molecule along with associated non-toxin proteins. Thus, the BoNt/A complex can be produced by Clostridial bacterium as 900 kD, 500 kD and 300 kD forms. BoNT/B and $C_1$ are apparently produced as only a 500 kD complex. BoNT/D is produced as both 300 kD and 500 kD complexes. Finally, BoNT/E and F are produced as only approximately 300 kD complexes. The complexes (i.e.

molecular weight greater than about 150 kD) are believed to contain a non-toxin hemaglutinin protein and a non-toxin and non-toxic nonhemaglutinin protein. These two non-toxin proteins (which along with the *botulinum* toxin molecule comprise the relevant neurotoxin complex) may act to provide stability against denaturation to the *botulinum* toxin molecule and protection against digestive acids when toxin is ingested. Additionally, it is possible that the larger (greater than about 150 kD molecular weight) *botulinum* toxin complexes may result in a slower rate of diffusion of the *botulinum* toxin away from a site of intramuscular injection of a *botulinum* toxin complex.

In vitro studies have indicated that *botulinum* toxin inhibits potassium cation induced release of both acetylcholine and norepinephrine from primary cell cultures of brainstem tissue. Additionally, it has been reported that *botulinum* toxin inhibits the evoked release of both glycine and glutamate in primary cultures of spinal cord neurons and that in brain synaptosome preparations *botulinum* toxin inhibits the release of each of the neurotransmitters acetylcholine, dopamine, norepinephrine, CGRP and glutamate.

BoNt/A can be obtained by establishing and growing cultures of *Clostridium botulinum* in a fermenter and then harvesting and purifying the fermented mixture in accordance with known procedures. All the *botulinum* toxin serotypes are initially synthesized as inactive single chain proteins which must be cleaved or nicked by proteases to become neuroactive. The bacterial strains that make *botulinum* toxin serotypes A and G possess endogenous proteases and serotypes A and G can therefore be recovered from bacterial cultures in predominantly their active form. In contrast, *botulinum* toxin serotypes $C_1$, D and E are synthesized by nonproteolytic strains and are therefore typically unactivated when recovered from culture. Serotypes B and F are produced by both proteolytic and nonproteolytic strains and therefore can be recovered in either the active or inactive form. However, even the proteolytic strains that produce, for example, the BoNt/B serotype only cleave a portion of the toxin produced. The exact proportion of nicked to unnicked molecules depends on the length of incubation and the temperature of the culture. Therefore, a certain percentage of any preparation of, for example, the BoNt/B toxin is likely to be inactive, possibly accounting for the known significantly lower potency of BoNt/B as compared to BoNt/A. The presence of inactive *botulinum* toxin molecules in a clinical preparation will contribute to the overall protein load of the preparation, which has been linked to increased antigenicity, without contributing to its clinical efficacy. Additionally, it is known that BoNt/B has, upon intramuscular injection, a shorter duration of activity and is also less potent than BoNt/A at the same dose level.

It has been reported that BoNt/A has been used in clinical settings as follows:

(1) about 75-125 units of BOTOX®[1] per intramuscular injection (multiple muscles) to treat cervical dystonia;

[1] Available from Allergan, Inc., of Irvine, Calif. under the tradename BOTOX®.

(2) 5-10 units of BOTOX® per intramuscular injection to treat glabellar lines (brow furrows) (5 units injected intramuscularly into the procerus muscle and 10 units injected intramuscularly into each corrugator supercilii muscle);

(3) about 30-80 units of BOTOX® to treat constipation by intrasphincter injection of the puborectalis muscle;

(4) about 1-5 units per muscle of intramuscularly injected BOTOX® to treat blepharospasm by injecting the lateral pre-tarsal orbicularis oculi muscle of the upper lid and the lateral pre-tarsal orbicularis oculi of the lower lid.

(5) to treat strabismus, extraocular muscles have been injected intramuscularly with between about 1-5 units of BOTOX®, the amount injected varying based upon both the size of the muscle to be injected and the extent of muscle paralysis desired (i.e. amount of diopter correction desired).

(6) to treat upper limb spasticity following stroke by intramuscular injections of BOTOX® into five different upper limb flexor muscles, as follows:
(a) flexor digitorum profundus: 7.5 U to 30 U
(b) flexor digitorum sublimus: 7.5 U to 30 U
(c) flexor carpi ulnaris: 10 U to 40 U
(d) flexor carpi radialis: 15 U to 60 U
(e) biceps brachii: 50 U to 200 U. Each of the five indicated muscles has been injected at the same treatment session, so that the patient receives from 90 U to 360 U of upper limb flexor muscle BOTOX® by intramuscular injection at each treatment session.

The success of BoNt/A to treat a variety of clinical conditions has led to interest in other *botulinum* toxin serotypes. A study of two commercially available BoNT/A preparations (BOTOX® and Dysport®) and preparations of BoNT/B and F (both obtained from Wako Chemicals, Japan) has been carried out to determine local muscle weakening efficacy, safety and antigenic potential. *Botulinum* toxin preparations were injected into the head of the right gastrocnemius muscle (0.5 to 200.0 units/kg) and muscle weakness was assessed using the mouse digit abduction scoring assay (DAS). $ED_{50}$ values were calculated from dose response curves. Additional mice were given intramuscular injections to determine $LD_{50}$ doses. The therapeutic index was calculated as $LD_{50}/ED_{50}$. Separate groups of mice received hind limb injections of BOTOX® (5.0 to 10.0 units/kg) or BoNt/B (50.0 to 400.0 units/kg), and were tested for muscle weakness and increased water consumption, the later being a putative model for dry mouth. Antigenic potential was assessed by monthly intramuscular injections in rabbits (1.5 or 6.5 ng/kg for BoNt/B or 0.15 ng/kg for BOTOX®). Peak muscle weakness and duration were dose related for all serotypes. DAS $ED_{50}$ values (units/kg) were as follows: BOTOX®: 6.7, Dysport®: 24.7, BoNt/B: 27.0 to 244.0, BoNT/F: 4.3. BOTOX® had a longer duration of action than BoNt/B or BoNt/F. Therapeutic index values were as follows: BOTOX®: 10.5, Dysport®: 6.3, BoNt/B: 3.2. Water consumption was greater in mice injected with BoNt/B than with BOTOX®, although BoNt/B was less effective at weakening muscles. After four months of injections 2 of 4 (where treated with 1.5 ng/kg) and 4 of 4 (where treated with 6.5 ng/kg) rabbits developed antibodies against BoNt/B. In a separate study, 0 of 9 BOTOX® treated rabbits demonstrated antibodies against BoNt/A. DAS results indicate relative peak potencies of BoNt/A being equal to BoNt/F, and BoNt/F being greater than BoNt/B. With regard to duration of effect, BoNt/A was greater than BoNt/B, and BoNt/B duration of effect was greater than BoNt/F. As shown by the therapeutic index values, the two commercial preparations of BoNt/A (BOTOX® and Dysport®) are different. The increased water consumption behavior observed following hind limb injection of BoNt/B indicates that clinically significant amounts of this serotype entered the murine systemic circulation. The results also indicate that in order to achieve efficacy comparable to BoNt/A, it is necessary to increase doses of the other serotypes examined. Increased dosage can comprise safety. Furthermore, in rabbits, serotype B was more antigenic than was BOTOX®, possibly because of the higher protein load injected to achieve an effective dose of BoNt/B.

The tetanus neurotoxin acts mainly in the central nervous system, while *botulinum* neurotoxin acts at the neuromuscular junction; both act by inhibiting acetylcholine release from the axon of the affected neuron into the synapse, resulting in paralysis. The effect of intoxication on the affected neuron is long-lasting and until recently has been thought to be irreversible. The tetanus neurotoxin is known to exist in one immunologically distinct serotype.

Acetylcholine

Typically only a single type of small molecule neurotransmitter is released by each type of neuron in the mammalian nervous system. The neurotransmitter acetylcholine is secreted by neurons in many areas of the brain, but specifically by the large pyramidal cells of the motor cortex, by several different neurons in the basal ganglia, by the motor neurons that innervate the skeletal muscles, by the preganglionic neurons of the autonomic nervous system (both sympathetic and parasympathetic), by the postganglionic neurons of the parasympathetic nervous system, and by some of the postganglionic neurons of the sympathetic nervous system. Essentially, only the postganglionic sympathetic nerve fibers to the sweat glands, the piloerector muscles and a few blood vessels are cholinergic and most of the postganglionic neurons of the sympathetic nervous system secret the neurotransmitter norepinephine. In most instances acetylcholine has an excitatory effect. However, acetylcholine is known to have inhibitory effects at some of the peripheral parasympathetic nerve endings, such as inhibition of the heart by the vagal nerve.

The efferent signals of the autonomic nervous system are transmitted to the body through either the sympathetic nervous system or the parasympathetic nervous system. The preganglionic neurons of the sympathetic nervous system extend from preganglionic sympathetic neuron cell bodies located in the intermediolateral horn of the spinal cord. The preganglionic sympathetic nerve fibers, extending from the cell body, synapse with postganglionic neurons located in either a paravertebral sympathetic ganglion or in a prevertebral ganglion. Since, the preganglionic neurons of both the sympathetic and parasympathetic nervous system are cholinergic, application of acetylcholine to the ganglia will excite both sympathetic and parasympathetic postganglionic neurons.

Acetylcholine activates two types of receptors, muscarinic and nicotinic receptors. The muscarinic receptors are found in all effector cells stimulated by the postganglionic neurons of the parasympathetic nervous system, as well as in those stimulated by the postganglionic cholinergic neurons of the sympathetic nervous system. The nicotinic receptors are found in the synapses between the preganglionic and postganglionic neurons of both the sympathetic and parasympathetic. The nicotinic receptors are also present in many membranes of skeletal muscle fibers at the neuromuscular junction.

Acetylcholine is released from cholinergic neurons when small, clear, intracellular vesicles fuse with the presynaptic neuronal cell membrane. A wide variety of non-neuronal secretory cells, such as, adrenal medulla (as well as the PC12 cell line) and pancreatic islet cells release catecholamines and insulin, respectively, from large dense-core vesicles. The PC12 cell line is a clone of rat pheochromocytoma cells extensively used as a tissue culture model for studies of sympathoadrenal development. *Botulinum* toxin inhibits the release of both types of compounds from both types of cells in vitro, permeabilized (as by electroporation) or by direct injection of the toxin into the denervated cell. *Botulinum* toxin is also known to block release of the neurotransmitter glutamate from cortical synaptosomes cell cultures.

Sanders et al. in U.S. Pat. No. 5,766,605 disclose that BoNT/A can be used to treat autonomic nervous system disorders, for example rhinorrhea, otitis media, excessive salivation, asthma, chronic obstructive pulmonary disease (COPD), excessive stomach acid secretion, spastic colitis and excessive sweating.

Furthermore, Binder U.S. Pat. No. 5,714,468 discloses that BoNT/A can be used to treat migraine headache pain that is associated with muscle spasm, vascular disturbances, neuralgia and neuropathy. Additionally, our laboratory data obtained from experiments with rats show that pain, particularly inflammation pain, may be reduced with an injection of *botulinum* serotype A, either spinally or peripherally.

One of the reasons that BoNT/A has been selected over the other serotypes, for example serotypes B, $C_1$, D, E, F, and G, for clinical use is that BoNT/A has a substantially longer lasting therapeutic effect. In other words, the inhibitory effect of BoNT/A is more persistent. Therefore, the other serotypes of *botulinum* toxins could potentially be effectively used in a clinical environment if their biological persistence could be enhanced. For example, parotid sialocele is a condition where the patient suffers from excessive salivation. Sanders et al. disclose in their patent that serotype D may be very effective in reducing excessive salivation. However, the biological persistence of serotype D *botulinum* toxin is relatively short and thus may not be practical for clinical use. If the biological persistence of serotype D may be enhanced, it may effectively be used in a clinical environment to treat, for example, parotid sialocele.

Another reason that BoNT/A has been a preferred neurotoxin for clinical use is, as discussed above, its superb ability to immobilize muscles through flaccid paralysis. For example, BoNT/A is preferentially used to immobilize muscles and prevent limb movements after a tendon surgery to facilitate recovery. However, for some minor tendon surgeries, the healing time is relatively short. It would be beneficial to have a BoNT/A without the prolonged persistence for use in such circumstances so that the patient can regain mobility at about the same time they recover from the surgery.

There is a need to have modified neurotoxins that are non serotype A *botulinum* toxins with enhanced biological persistence and modified neurotoxins that are BoNT/A with reduced biological persistence and methods for preparing such toxins.

SUMMARY

The present invention meets this need and provides for non serotype A *botulinum* toxins with enhanced persistence and BoNT/A with reduced persistence and methods for preparing such toxins.

In one broad embodiment of the invention, a modified neurotoxin is formed from a neurotoxin which includes a structural modification. The structural modification is able to alter the biological persistence of the neurotoxin. In one embodiment, the structural modification includes fusing a biological persistence enhancing component with a neurotoxin. The biological persistence enhancing component increases the duration of the inhibitory effect of the modified neurotoxin intracellularly. Preferably, the biological persistence enhancing component is a leucine-based motif.

Without wishing to be limited by any particular theory or mechanism of operation, it is believed that the leucine-based motif enhances the persistence of a neurotoxin by increasing its biological half-life. For example, it is known that BoNT/A has a very long biological persistence. Keller et al., *FEBS Letters*, 456:137-142 (1999), investigated to determine whether the persistence of BoNT/A is due to a depressed synthesis of SNAP-25 to replace the cleaved ones, or is due to the stability of the light chain intracellularly. Keller et al. found that the major factor limiting cellular recovery is the prolonged stability of toxin, or prolonged half-life.

Furthermore, without wishing to be limited by any particular theory or mechanism of operation, it is believed that the leucine-based motif located on the light chain, or the third amino acid sequence region, of BoNT/A, and not on any other serotypes, is responsible for the prolonged half-life of BoNT/A.

A leucine-based motif is often found on the carboxyl termini of several membrane receptors and vesicular neurotransmitter transporter and it apparently plays a crucial role in vesicle/membrane trafficking. Liu et al. *Trends Cell Biol*, 9:356-363 (1999); Tan et al. *J Biol Chem*, 273:17351-17360 (1998); Dietrich et al. *J. Cell Bio*, 138:271-281 (1997); Shin et al. *J Biol Chem*, 266:10658-10665 (1991) and Geisler et al. *J Biol Chem*, 273:21316-21323 (1998). More specifically, the leuine-based motif is found in a membrane-proximal, cytoplasmic, carboxylic terminal tail of a membrane-bound receptor or transporter protein. It has been demonstrated that adaptor proteins that are highly concentrated at clathrin coated pits bind to the leucine-based motif and that disruption of this motif disrupts endocytosis of the motif-containing protein. Tan et al. *J Biol Chem*, 273:17351-17360 (1998); Dietrich et al. *J. Cell Bio*, 138:271-281 (1997) and Shin et al. *J Biol Chem*, 266:10658-10665 (1991). Furthermore, addition of the leucine-based motif to the carboxyl terminus of the plasma membrane protein Tac resulted in endocytosis of the chimera, suggesting that the motif is sufficient for targeted endocytosis. Tan et al. Supra.

The leucine-based motif located on the light chain of BoNT/A may cause the light chain to localize at the membranes, similarly to how membrane-bound receptor or transporter protein are localized at the membranes described above. Localization of the light chain to the membrane may protect and preserve the light chain, and the heavy chain if it is still attached, from being removed and/or degraded by the intracellular cleaning processes, thereby rendering it a long biological half-life. For example, intracellular autophagosomes are responsible for cleaning the cytoplasm by engulfing, and thereafter degrading, free floating foreign substances in the cytoplasm. Erdal et al. *Naunyn Schmiedebergs Acrch Pharmacol*, 351:67-78 (1995). Since the leucine-based motif provides an anchor for the light chain, and the heavy chain if it is still attached, it would be difficult for the autophagosomes to remove and engulf the light chain from the cytoplasm. Thus the light chain remains in the cytoplasm to continue exerting its inhibitory effects on vesicular exocytosis of neurotransmitters.

In another embodiment, the leucine-based motif located on the light chain of BoNT/A is removed in its entirety or in parts. This modified neurotoxin effectively has a shortened the biological persistence. Preferably, this modified neurotoxin has a decreased half-life.

This invention also provide for methods of producing modified neurotoxins. Additionally, this invention provide for methods of using the modified neurotoxins to treat biological disorders.

Definitions

Before proceeding to describe the present invention, the following definitions are provided and apply herein.

"Heavy chain" means the heavy chain of a clostridial neurotoxin. It preferably has a molecular weight of about 100 kDa and may be referred to herein as H chain or as H.

"$H_N$" means a fragment (preferably having a molecular weight of about 50 kDa) derived from the H chain of a Clostridial neurotoxin which is approximately equivalent to the amino terminal segment of the H chain, or the portion corresponding to that fragment in the intact in the H chain. It is believed to contain the portion of the natural or wild type clostridial neurotoxin involved in the translocation of the L chain across an intracellular endosomal membrane.

"$H_C$" means a fragment (about 50 kDa) derived from the H chain of a clostridial neurotoxin which is approximately equivalent to the carboxyl terminal segment of the H chain, or the portion corresponding to that fragment in the intact H chain. It is believed to be immunogenic and to contain the portion of the natural or wild type Clostridial neurotoxin involved in high affinity, presynaptic binding to motor neurons.

"Light chain" means the light chain of a clostridial neurotoxin. It preferably has a molecular weight of about 50 kDa, and can be referred to as L chain, L or as the proteolytic domain (amino acid sequence) of a clostridial neurotoxin. The light chain is believed to be effective as an inhibitor of neurotransmitter release when it is released into a cytoplasm of a target cell.

"Neurotoxin" means a molecule that is capable of interfering with the functions of a neuron. The "neurotoxin" may be naturally occurring or man-made.

"Modified neurotoxin" means a neurotoxin which includes a structural modification. In other words, a "modified neurotoxin" is a neurotoxin which has been modified by a structural modification. The structural modification changes the biological persistence, preferably the biological half-life, of the modified neurotoxin relative to the neurotoxin from which the modified neurotoxin is made. The modified neurotoxin is structurally different from a naturally existing neurotoxin.

"Structural modification" means a physical change to the neurotoxin that may be affected by covalently fusing one or more amino acids to the neurotoxin. "Structural modification" also means the deletion of one or more amino acids from a neurotoxin. Furthermore, "structural modification" may also mean any changes to a neurotoxin that makes it physically or chemically different from an identical neurotoxin without the structural modification.

"Biological persistence" means the time duration in which a neurotoxin or a modified neurotoxin causes an interference with a neuronal function, for example the time duration in which a neurotoxin or a modified neurotoxin causes a substantial inhibition of the release of acetylcholine from a nerve terminal.

"Biological half-life" means the time that the concentration of a neurotoxin or a modified neurotoxin, preferably the active portion of the neurotoxin or modified neurotoxin, for example the light chain of *botulinum* toxins, is reduced to half of the original concentration in a mammal, preferably in the neurons of the mammal.

DETAILED DESCRIPTION

The present invention is based upon the discovery that the biological persistence of a neurotoxin may be altered by structurally modifying the neurotoxin. In other words, a modified neurotoxin with an altered biological persistence may be formed from a neurotoxin containing or including a structural modification. In one embodiment, the structural modification includes the fusing a biological persistence enhancing component to the primary structure of a neurotoxin to enhance its biological persistence. In a preferred embodiment, the biological persistence enhancing component is a leucine-based motif. Preferably, the biological persistence enhancing component enhances the biological half-life of the modified neurotoxin. More preferably, the biological half-life of the modified neurotoxin is enhanced by about 10%. Even more preferably, the biological half-life of the modified neurotoxin is enhanced by about 100%. Generally speaking, the modified neurotoxin has a biological persistence of about 20% to 300% more than an identical neurotoxin without the structural modification. That is, for example, the modified neurotoxin including the biological persistence enhancing component is able to cause a substantial inhibition of acetylcholine release from a nerve terminal for about 20% to about 300% longer than a neurotoxin that is not modified.

In a broad embodiment of the present invention, a leucine-based motif is an oligomer of seven amino acids. The oligomer is organized in to two groups. The first five amino acids starting from the amino terminal of the leucine-based motif form a "quintet of amino acids." The two amino acids immediately following the quintet of amino acids form a "duplet of amino acids." In a preferred embodiment, the duplet of amino acids is located at the carboxyl terminal region of the leucine-based motif. In another preferred embodiment, the quintet of amino acids includes at least one acidic amino acid selected from a group consisting of a glutamate and an aspartate.

The duplet of amino acid includes at least one hydrophobic amino acid, for example leucine, isoleucine, methionine, alanine, phenylalanine, tryptophan, valine or tyrosine. Preferably, the duplet of amino acid is a leucine-leucine, a leucine-isoleucine, an isoleucine-leucine or an isoleucine-isoleucine. Even more preferably, the duplet is a leucine-leucine.

In one embodiment, the leucine-based motif is XDXXXLL (SEQ ID NO: 1), wherein x and may be any amino acids. In another embodiment, the leucine-based motif is XEXXXLL (SEQ ID NO: 2), wherein E is glutamic acid. In another embodiment, the duplet of amino acids may include an isoleucine or a methionine, forming XDXXXLI (SEQ ID NO: 3) or XDXXXLM (SEQ ID NO: 4), respectively. Additionally, the aspartic acid, D, may be replaced by a glutamic acid, E, to form XEXXXLI (SEQ ID NO: 5) and XEXXXLM (SEQ ID NO: 6). In a preferred embodiment, the leucine-based motif is SEQ ID NO: 7.

In another embodiment, the quintet of amino acids comprises at least one hydroxyl containing amino acid, for example a serine, a threonine or a tyrosine. Preferably, the hydroxyl containing amino acid can be phosphorylated. More preferably, the hydroxyl containing amino acid is a serine which can be phosphorylated to allow for the binding of adaptor proteins.

Although non-modified amino acids are provided as examples, a modified amino acid is also contemplated to be within the scope of this invention. For example, leucine-based motif may include a halogenated, preferably, fluorinated leucine.

Various leucine-based motif are found in various species. A list of possible leucine-based motif derived from the various species that may be used in accordance with this invention is shown in Table 1. This list is not intended to be limiting.

TABLE 1

| Species | Sequence | SEQ ID NO: |
|---|---|---|
| BoNT/A | FEFYKLL | 7 |
| Rat VMAT1 | EEKRAIL | 8 |
| Rat VMAT 2 | EEKMAIL | 9 |
| Rat VAChT | SERDVLL | 10 |

TABLE 1-continued

| Species | Sequence | SEQ ID NO: |
|---|---|---|
| Rat δ | VDTQVLL | 11 |
| Mouse δ | AEVQALL | 12 |
| Frog γ/δ | SDKQNLL | 13 |
| Chicken γ/δ | SDRQNLI | 14 |
| Sheep δ | ADTQVLM | 15 |
| Human CD3γ | SDKQTLL | 16 |
| Human CD4 | SQIKRLL | 17 |
| Human δ | ADTQALL | 18 |

VMAT is vesicular monoamine transporter; VACht is vesicular acetylcholine transporter. Italicized serine residues are potential sites of phosphorylation.

The modified neurotoxin may be formed from any neurotoxin. Preferably, the neurotoxin used is a Clostridial neurotoxin. A Clostridial neurotoxin comprises a polypeptide having three amino acid sequence regions. The first amino acid sequence region includes a neuronal binding moiety which is substantially completely derived from a neurotoxin selected from a group consisting of beratti toxin; butyricum toxin; tetani toxin; BoNT/A, B, $C_1$, D, E, F, and G. Preferably, the first amino acid sequence region is derived from the carboxyl terminal region of a toxin heavy chain, $H_C$.

The second amino acid sequence region is effective to translocate the polypeptide or a part thereof across an endosome membrane into the cytoplasm of a neuron. In one embodiment, the second amino acid sequence region of the polypeptide comprises an amine terminal of a heavy chain, $H_N$, derived from a neurotoxin selected from a group consisting of beratti toxin; butyricum toxin; tetani toxin; BoNT/A, B, $C_1$, D, E, F, and G.

The third amino acid sequence region has therapeutic activity when it is released into the cytoplasm of a target cell or neuron. In one embodiment, the third amino acid sequence region of the polypeptide comprises a toxin light chain, L, derived from a neurotoxin selected from a group consisting of beratti toxin; butyricum toxin; tetani toxin; BoNT/A, B, $C_1$, D, E, F, and G.

The Clostridial neurotoxin may be a hybrid neurotoxin. For example, each of the neurotoxin's amino acid sequence regions may be derived from a different Clostridial neurotoxin serotype. For example, in one embodiment, the polypeptide comprises a first amino acid sequence region derived from the $H_C$ of the tetani toxin, a second amino acid sequence region derived from the $H_N$ of BoNt/B, and a third amino acid sequence region derived from the L chain of *botulinum* serotype E. All other possible combinations are included within the scope of the present invention.

Alternatively, all three of the amino acid sequence regions of the Clostridial neurotoxin may be from the same species and same serotype. If all three amino acid sequence regions of the neurotoxin are from the same Clostridial neurotoxin species and serotype, the neurotoxin will be referred to by the species and serotype name. For example, a neurotoxin polypeptide may have its first, second and third amino acid sequence regions derived from BoNT/E. In which case, the neurotoxin is referred as BoNT/E.

Additionally, each of the three amino acid sequence regions may be modified from the naturally occurring sequence from which they are derived. For example, the amino acid sequence region may have at least one or more amino acid may be added or deleted as compared to the naturally occurring sequence.

The biological persistence enhancing component, preferably the leucine-based motif, may be fused with any of the above described neurotoxin to form a modified neurotoxin with an enhanced biological persistence. "Fusing" as used in the context of this invention includes covalently adding to or covalently inserting in between a primary structure of a neurotoxin. Preferably, the biological persistence enhancing component is added to a Clostridial neurotoxin which does not have a leucine-based motif in its primary structure. For example, in one embodiment, the leucine-based motif is fused with a hybrid neurotoxin, wherein the third amino acid sequence is not derived from *botulinum* serotype A. In another embodiment, the leucine-based motif is fused with a BoNt/E.

In one embodiment, the leucine-based motif is fused with the third amino acid sequence region of the neurotoxin. In a preferred embodiment, the leucine-based motif is fused with the region towards the carboxylic terminal of the third amino acid sequence region. More preferably, the leucine-based motif is fused with the carboxylic terminal of the third region of a neurotoxin. Even more preferably, the leucine-based motif is fused with the carboxylic terminal of the third region of BoNt/E.

In another embodiment, the structural modification of a neurotoxin which has a preexisting leucine-based motif includes deleting one or more amino acids from the leucine-based motif. Alternatively, a modified neurotoxin includes a structural modification which results in a neurotoxin with one or more amino acids absent from the leucine-based motif. The removal of one or more amino acids from the preexisting leucine-based motif is effective to reduce the biological persistence of a modified neurotoxin. More preferably, the deletion of one or more amino acids from the leucine-based motif of BoNT/A reduces the biological half-life of the modified neurotoxin.

In one broad aspect of the present invention, a method is provided for treating a biological disorder using a modified neurotoxin. The treatments may include treating neuromuscular disorders, autonomic nervous system disorders and pain.

The neuromuscular disorders and conditions that may be treated with a modified neurotoxin include: for example, strabismus, blepharospasm, spasmodic torticollis (cervical dystonia), oromandibular dystonia and spasmodic dysphonia (largyngeal dystonia).

For example, Borodic U.S. Pat. No. 5,053,005 discloses methods for treating juvenile spinal curvature, i.e. scoliosis, using BoNT/A. The disclosure of Borodic is incorporated in its entirety herein by reference. In one embodiment, using substantially similar methods as disclosed by Borodic, a modified neurotoxin is administered to a mammal, preferably a human, to treat spinal curvature. In a preferred embodiment, a modified neurotoxin comprising BoNT/E fused with a leucine-based motif is administered. Even more preferably, a modified neurotoxin comprising BoNT/E with a leucine-based motif fused to the carboxyl terminal of its light chain is administered to the mammal, preferably a human, to treat spinal curvature. The modified neurotoxin may be administered to treat other neuromuscular disorders using well known techniques that are commonly performed with BoNT/A.

Autonomic nervous system disorders may also be treated with a modified neurotoxin. For example, glandular malfunctioning is an autonomic nervous system disorder. Glandular malfunctioning includes excessive sweating and excessive salivation. Respiratory malfunctioning is another example of an autonomic nervous system disorder. Respiratory malfunctioning includes chronic obstructive pulmonary disease and asthma. Sanders et al. discloses methods for treating the autonomic nervous system, such as excessive sweating, excessive salivation, asthma, etc., using naturally existing *botulinum* toxins. The disclosure of Sander et al. is incorporated in its entirety by reference herein. In one embodiment, substantially similar methods to that of Sanders et al. may be employed, but using a modified neurotoxin, to treat autonomic nervous system disorders such as the ones discussed above. For example, a modified neurotoxin may be locally applied to the nasal cavity of the mammal in an amount sufficient to degenerate cholinergic neurons of the autonomic nervous system that control the mucous secretion in the nasal cavity.

Pain that may be treated by a modified neurotoxin include pain caused by muscle tension, or spasm, or pain that is not associated with muscle spasm. For example, Binder in U.S. Pat. No. 5,714,468 discloses that headache caused by vascular disturbances, muscular tension, neuralgia and neuropathy may be treated with a naturally occurring *botulinum* toxin, for example BoNT/A. The disclosures of Binder is incorporated in its entirety herein by reference. In one embodiment, substantially similar methods to that of Binder may be employed, but using a modified neurotoxin, to treat headache, especially the ones caused by vascular disturbances, muscular tension, neuralgia and neuropathy. Pain caused by muscle spasm may also be treated by an administration of a modified neurotoxin. For example, a BoNT/E fused with a leucine-based motif, preferably at the carboxyl terminal of the BoNT/E light chain, may be administered intramuscularly at the pain/spasm location to alleviate pain.

Furthermore, a modified neurotoxin may be administered to a mammal to treat pain that is not associated with a muscular disorder, such as spasm. In one broad embodiment, methods of the present invention to treat non-spasm related pain include central administration or peripheral administration of the modified neurotoxin.

For example, Foster et al. in U.S. Pat. No. 5,989,545 discloses that a *botulinum* toxin conjugated with a targeting moiety may be administered centrally (intrathecally) to alleviate pain. The disclosures of Foster et al. is incorporated in its entirety by reference herein. In one embodiment, substantially similar methods to that of Foster et al. may be employed, but using the modified neurotoxin according to this invention, to treat pain. The pain to be treated may be an acute pain, or preferably, chronic pain.

An acute or chronic pain that is not associated with a muscle spasm may also be alleviated with a local, peripheral administration of the modified neurotoxin to an actual or a perceived pain location on the mammal. In one embodiment, the modified neurotoxin is administered subcutaneously at or near the location of pain, for example at or near a cut. In another embodiment, the modified neurotoxin is administered intramuscularly at or near the location of pain, for example at or near a bruise location on the mammal. In another embodiment, the modified neurotoxin is injected directly into a joint of a mammal, for treating or alleviating pain cause arthritis conditions. Also, frequent repeated injections or infusion of the modified neurotoxin to a peripheral pain location is within the scope of the present invention. However, given the long lasting therapeutic effects of the present invention, frequent injections or infusion of the neurotoxin may not be necessary. For example, practice of the present invention can provide an analgesic effect, per injection, for 2 months or longer, for example 27 months, in humans.

Without wishing to limit the invention to any mechanism or theory of operation, it is believed that when the modified neurotoxin is administered locally to a peripheral location, it inhibits the release of neuro-substances, for example substance P, from the peripheral primary sensory terminal. Since the release of substance P by the peripheral primary sensory terminal may cause or at least amplify pain transmission process, inhibition of its release at the peripheral primary sensory terminal will dampen the transmission of pain signals from reaching the brain.

In addition to having pharmacologic actions at the peripheral location, the modified neurotoxin of the present invention may also have inhibitory effects in the central nervous system. Presumably the retrograde transport is via the primary afferent. This hypothesis is supported by our experimental data which shows that BoNT/A is retrograde transported to the dorsal horn when the neurotoxin is injected peripherally. Moreover, work by Weigand et al, *Nauny-Schmiedeberg's Arch. Pharmacol.* 1976; 292, 161-165, and Habermann, *Nauny-Schmiedeberg's Arch. Pharmacol.* 1974; 281, 47-56, showed that *botulinum* toxin is able to ascend to the spinal area by retrograde transport. As such, a modified neurotoxin, for example BoNt/A with one or more amino acids deleted from the leucine-based motif, injected at a peripheral location, for example intramuscularly, may be retrograde transported from the peripheral primary sensory terminal to the central primary sensory terminal.

The amount of the modified neurotoxin administered can vary widely according to the particular disorder being treated, its severity and other various patient variables including size, weight, age, and responsiveness to therapy. Generally, the dose of modified neurotoxin to be administered will vary with the age, presenting condition and weight of the mammal, preferably a human, to be treated. The potency of the modified neurotoxin will also be considered.

Assuming a potency which is substantially equivalent to $LD_{50}=2,730$ U in a human patient and an average person is 75 kg, a lethal dose would be about 36 U/kg of a modified neurotoxin. Therefore, when a modified neurotoxin with such an $LD_{50}$ is administered, it would be appropriate to administer less than 36 U/kg of the modified neurotoxin into human subjects. Preferably, about 0.01 U/kg to 30 U/kg of the modified neurotoxin is administered. More preferably, about 1 U/kg to about 15 U/kg of the modified neurotoxin is administered. Even more preferably, about 5 U/kg to about 10 U/kg modified neurotoxin is administered. Generally, the modified neurotoxin will be administered as a composition at a dosage that is proportionally equivalent to about 2.5 cc/100 U. Those of ordinary skill in the art will know, or can readily ascertain, how to adjust these dosages for neurotoxin of greater or lesser potency.

Although examples of routes of administration and dosages are provided, the appropriate route of administration and dosage are generally determined on a case by case basis by the attending physician. Such determinations are routine to one of ordinary skill in the art (see for example, *Harrison's Principles of Internal Medicine* (1998), edited by Anthony Fauci et al., 14$^{th}$ edition, published by McGraw Hill). For example, the route and dosage for administration of a modified neurotoxin according to the present disclosed invention can be selected based upon criteria such as the solubility characteristics of the modified neurotoxin chosen as well as the types of disorder being treated.

The modified neurotoxin may be produced by chemically linking the leucine-based motif to a neurotoxin using conventional chemical methods well known in the art. The neurotoxin may be obtained from a harvesting neurotoxins. For example, BoNt/E can be obtained by establishing and growing cultures of *Clostridium botulinum* in a fermenter and then harvesting and purifying the fermented mixture in accordance with known procedures. All the *botulinum* toxin serotypes are initially synthesized as inactive single chain proteins which must be cleaved or nicked by proteases to become neuroactive. The bacterial strains that make *botulinum* toxin serotypes A and G possess endogenous proteases and serotypes A and G can therefore be recovered from bacterial cultures in predominantly their active form. In contrast, *botulinum* toxin serotypes $C_1$, D and E are synthesized by non-proteolytic strains and are therefore typically unactivated when recovered from culture. Serotypes B and F are produced by both proteolytic and nonproteolytic strains and therefore can be recovered in either the active or inactive form. However, even the proteolytic strains that produce, for example, the BoNt/B serotype only cleave a portion of the toxin produced. The exact proportion of nicked to unnicked molecules depends on the length of incubation and the temperature of the culture. Therefore, a certain percentage of any preparation of, for example, the BoNt/B toxin is likely to be inactive, possibly accounting for the known significantly lower potency of BoNt/B as compared to BoNt/A. The presence of inactive *botulinum* toxin molecules in a clinical preparation will contribute to the overall protein load of the preparation, which has been linked to increased antigenicity, without contributing to its clinical efficacy. Additionally, it is known that BoNt/B has, upon intramuscular injection, a shorter duration of activity and is also less potent than BoNt/A at the same dose level.

The modified neurotoxin may also be produced by recombinant techniques. Recombinant techniques are preferable for producing a neurotoxin having amino acid sequence regions from different Clostridial species or having modified amino acid sequence regions. Also, the recombinant technique is preferable in producing BoNT/A with the leucine-based motif being modified by deletion. The technique includes steps of obtaining genetic materials from natural sources, or synthetic sources, which have codes for a neuronal binding moiety, an amino acid sequence effective to translocate the neurotoxin or a part thereof, and an amino acid sequence having therapeutic activity when released into a cytoplasm of a target cell, preferably a neuron. In a preferred embodiment, the genetic materials have codes for the biological persistence enhancing component, preferably the leucine-based motif, the $H_C$, the $H_N$ and the L chain of the Clostridial neurotoxins and fragments thereof. The genetic constructs are incorporated into host cells for amplification by first fusing the genetic constructs with a cloning vectors, such as phages or plasmids. Then the cloning vectors are inserted into hosts, preferably *E. coli*'s. Following the expressions of the recombinant genes in host cells, the resultant proteins can be isolated using conventional techniques.

There are many advantages to producing these modified neurotoxins recombinantly. For example, to form a modified neurotoxin, a modifying fragment must be attached or inserted into a neurotoxin. The production of neurotoxin from anaerobic *Clostridium* cultures is a cumbersome and time-consuming process including a multi-step purification protocol involving several protein precipitation steps and either prolonged and repeated crystallization of the toxin or several stages of column chromatography. Significantly, the high toxicity of the product dictates that the procedure must be performed under strict containment (BL-3). During the fermentation process, the folded single-chain neurotoxins are activated by endogenous clostridial proteases through a process termed nicking to create a dichain. Sometimes, the process of nicking involves the removal of approximately 10 amino acid residues from the single-chain to create the dichain form in which the two chains remain covalently linked through the intrachain disulfide bond.

The nicked neurotoxin is much more active than the unnicked form. The amount and precise location of nicking varies with the serotypes of the bacteria producing the toxin. The differences in single-chain neurotoxin activation and, hence, the yield of nicked toxin, are due to variations in the serotype and amounts of proteolytic activity produced by a given strain. For example, greater than 99% of *Clostridial botulinum* serotype A single-chain neurotoxin is activated by the Hall A *Clostridial botulinum* strain, whereas serotype B and E strains produce toxins with lower amounts of activation (0 to 75% depending upon the fermentation time). Thus, the high toxicity of the mature neurotoxin plays a major part in the commercial manufacture of neurotoxins as therapeutic agents.

The degree of activation of engineered clostridial toxins is, therefore, an important consideration for manufacture of these materials. It would be a major advantage if neurotoxins such as *botulinum* toxin and tetanus toxin could be expressed, recombinantly, in high yield in rapidly-growing bacteria (such as heterologous *E. coli* cells) as relatively non-toxic single-chains (or single chains having reduced toxic activity) which are safe, easy to isolate and simple to convert to the fully-active form.

With safety being a prime concern, previous work has concentrated on the expression in *E. coli* and purification of individual H and L chains of tetanus and *botulinum* toxins; these isolated chains are, by themselves, non-toxic; see Li et al., *Biochemistry* 33:7014-7020 (1994); Zhou et al., *Biochemistry* 34:15175-15181 (1995), hereby incorporated by reference herein. Following the separate production of these peptide chains and under strictly controlled conditions the H and L chains can be combined by oxidative disulphide linkage to form the neuroparalytic di-chains.

EXAMPLES

The following non-limiting examples provide those of ordinary skill in the art with specific preferred methods to treat non-spasm related pain within the scope of the present invention and are not intended to limit the scope of the invention.

Example 1

Treatment of Pain Associated with Muscle Disorder

An unfortunate 36 year old woman has a 15 year history of temporomandibular joint disease and chronic pain along the masseter and temporalis muscles. Fifteen years prior to evaluation she noted increased immobility of the jaw associated with pain and jaw opening and closing and tenderness along each side of her face. The left side is originally thought to be worse than the right. She is diagnosed as having temporomandibular joint (TMJ) dysfunction with subluxation of the joint and is treated with surgical orthoplasty meniscusectomy and condyle resection.

She continues to have difficulty with opening and closing her jaw after the surgical procedures and for this reason, several years later, a surgical procedure to replace prosthetic joints on both sides is performed. After the surgical procedure progressive spasms and deviation of the jaw ensues. Further surgical revision is performed subsequent to the original operation to correct prosthetic joint loosening. The jaw continues to exhibit considerable pain and immobility after these surgical procedures. The TMJ remained tender as well as the muscle itself. There are tender points over the temporomandibular joint as well as increased tone in the entire muscle. She is diagnosed as having post-surgical myofascial pain syndrome and is injected with 7 U/kg of the modified neurotoxin into the masseter and temporalis muscles, preferably the modified neurotoxin is BoNT/E fused with a leucine-based motif.

Several days after the injections she noted substantial improvement in her pain and reports that her jaw feels looser. This gradually improves over a 2 to 3 week period in which she notes increased ability to open the jaw and diminishing pain. The patient states that the pain is better than at any time in the last 4 years. The improved condition persists for up to 27 months after the original injection of the modified neurotoxin.

Example 2

Treatment of Pain Subsequent to Spinal Cord Injury

A patient, age 39, experiencing pain subsequent to spinal cord injury is treated by intrathecal administration, for example by spinal tap or by catherization (for infusion), to the spinal cord, with between about 0.1 U/kg of the modified neurotoxin, preferably the modified neurotoxin is BoNT/E fused with a leucine-based motif. The particular toxin dose and site of injection, as well as the frequency of toxin administrations depend upon a variety of factors within the skill of the treating physician, as previously set forth. Within about 1 to about 7 days after the modified neurotoxin administration, the patient's pain is substantially reduced. The pain alleviation persists for up to 27 months.

Example 3

Peripheral Administration of a Modified Neurotoxin to Treat "Shoulder-Hand Syndrome"

Pain in the shoulder, arm, and hand can develop, with muscular dystrophy, osteoporosis, and fixation of joints. While most common after coronary insufficiency, this syndrome may occur with cervical osteoarthritis or localized shoulder disease, or after any prolonged illness that requires the patient to remain in bed.

A 46 year old woman presents a shoulder-hand syndrome type pain. The pain is particularly localized at the deltoid region. The patient is treated by a bolus injection of between about 0.05 U/kg to about 2 U/kg of a modified neurotoxin subcutaneously to the shoulder, preferably the modified neurotoxin is BoNT/E fused with a leucine-based motif. The particular dose as well as the frequency of administrations depends upon a variety of factors within the skill of the treating physician, as previously set forth. Within 1-7 days after modified neurotoxin administration the patient's pain is substantially alleviated. The duration of the pain alleviation is from about 7 to about 27 months.

Example 4

Peripheral Administration of a Modified Neurotoxin to Treat Postherpetic Neuralgia Postherpetic neuralgia is one of the most intractable of chronic pain problems. Patients suffering this excruciatingly painful process often are elderly, have debilitating disease, and are not suitable for major interventional procedures. The diagnosis is readily made by the appearance of the healed lesions of herpes and by the patient's history. The pain is intense and emotionally distressing. Postherpetic neuralgia may occur any where, but is most often in the thorax.

A 76 year old man presents a postherpetic type pain. The pain is localized to the abdomen region. The patient is treated by a bolus injection of between about 0.05 U/kg to about 2 U/kg of a modified neurotoxin intradermally to the abdomen, preferably the modified neurotoxin is BoNT/E fused with a leucine-based motif. The particular dose as well as the frequency of administrations depends upon a variety of factors within the skill of the treating physician, as previously set forth. Within 1-7 days after modified neurotoxin administration the patient's pain is substantially alleviated. The duration of the pain alleviation is from about 7 to about 27 months.

Example 5

Peripheral Administration of a Modified Neurotoxin to Treat Nasopharyngeal Tumor Pain These tumors, most often squamous cell carcinomas, are usually in the fossa of Rosenmuller and may invade the base of the skull. Pain in the face is common. It is constant, dull-aching in nature.

A 35 year old man presents a nasopharyngeal tumor type pain. Pain is found at the lower left cheek. The patient is treated by a bolus injection of between about 0.05 U/kg to about 2 U/kg of a modified neurotoxin intramuscularly to the cheek, preferably the modified neurotoxin is BoNT/E fused with a leucine-based motif. The particular dose as well as the frequency of administrations depends upon a variety of factors within the skill of the treating physician, as previously set forth. Within 1-7 days after modified neurotoxin administration the patient's pain is substantially alleviated. The duration of the pain alleviation is from about 7 to about 27 months.

Example 6

Peripheral Administration of a Modified Neurotoxin to Treat Inflammatory Pain

A patient, age 45, presents an inflammatory pain in the chest region. The patient is treated by a bolus injection of between about 0.05 U/kg to about 2 U/kg of a modified neurotoxin intramuscularly to the chest, preferably the modified neurotoxin is BoNT/E fused with a leucine-based motif. The particular dose as well as the frequency of administrations depends upon a variety of factors within the skill of the treating physician, as previously set forth. Within 1-7 days after modified neurotoxin administration the patient's pain is substantially alleviated. The duration of the pain alleviation is from about 7 to about 27 months.

Example 7

Treatment of Excessive Sweating

A male, age 65, with excessive unilateral sweating is treated by administering 0.05 U/kg to about 2 U/kg of a modified neurotoxin, depending upon degree of desired effect. Preferably the modified neurotoxin is BoNT/E fused with a leucine-based motif. The administration is to the gland nerve plexus, ganglion, spinal cord or central nervous system. The specific site of administration is to be determined by the physician's knowledge of the anatomy and physiology of the target glands and secretary cells. In addition, the appropriate spinal cord level or brain area can be injected with the toxin. The cessation of excessive sweating after the modified neurotoxin treatment is up to 27 months.

Example 8

Post Surgical Treatments

A female, age 22, presents a torn shoulder tendon and undergoes orthopedic surgery to repair the tendon. After the surgery, the patient is administered intramuscularly with about 0.05 U/kg to about 2 U/kg of a modified neurotoxin to the shoulder. Preferably, the modified neurotoxin is a BoNT/A wherein the leucine-based motif is removed. The specific site of administration is to be determined by the physician's knowledge of the anatomy and physiology of the muscles. The administered modified neurotoxin reduces movement of the arm to facilitate the recovery from the surgery. The effect of the modified neurotoxin is for about five weeks.

Example 9

Production of a Modified Neurotoxin with an Enhanced Biological Persistence

A modified neurotoxin may be produced by employing recombinant techniques in conjunction with conventional chemical techniques.

The neurotoxin that is to be fused with the leucine-based motif to form a modified neurotoxin may be produced recombinantly. The recombinant technique includes steps of obtaining genetic materials from either DNA cloned from natural sources, or synthetic oligonucleotide sequences, which have codes for a neurotoxin, preferably BoNT/E. The genetic constructs are incorporated into host cells for amplification by first fusing the genetic constructs with a cloning vectors, such as phages or plasmids. Then the cloning vectors are inserted into hosts, preferably *E. coli*'s. Following the expressions of the recombinant genes in host cells, the resultant proteins can be isolated using conventional techniques.

The neurotoxin, preferably BoNT/E, derived from the recombinant techniques can then be covalently fused with a leucine-based motif. Preferably, the leucine-based motif is fused to the light chain of BoNT/E at the carboxyl terminal. The fusion of the leucine-based motif with BoNT/E is achieved via chemical coupling using reagents and techniques known to those skilled in the art, for example PDPH/EDAC and Traut's reagent chemistry.

The modified neurotoxin produced according to this example has an enhanced biological persistence. Preferably, the biological persistence is enhanced by about 20% to about 300% relative to an identical neurotoxin without a leucine-based motif.

Example 10

Production of a Modified Neurotoxin with a Reduced Biological Persistence

A modified neurotoxin with a reduced biological persistence may be produced by employing recombinant techniques. The recombinant technique includes steps of obtaining genetic materials from a synthetic oligonucleotide sequences, which have codes for a neurotoxin, preferably BoNT/A, which does not have genetic codings for a leucine-based motif. The genetic constructs are incorporated into host cells for amplification by first fusing the genetic constructs with a cloning vectors, such as phages or plasmids. Then the cloning vectors are inserted into hosts, preferably *E. coli*'s. Following the expressions of the recombinant genes in host cells, the resultant proteins can be isolated using conventional techniques.

The modified neurotoxin produced according to this example has a reduced biological persistence. Preferably, the biological persistence is reduced by about 20% to about 300% relative to an identical neurotoxin, for example BoNT/A, with the leucine-based motif.

Although the present invention has been described in detail with regard to certain preferred methods, other embodiments, versions, and modifications within the scope of the present invention are possible. For example, a wide variety of modified neurotoxins can be effectively used in the methods of the present invention in place of clostridial neurotoxins. Also, the corresponding genetic codes, i.e. DNA sequence, to the modified neurotoxins are also considered to be part of this invention. Additionally, the present invention includes peripheral administration methods wherein two or more modified neurotoxins, for example BoNT/E with a fused leucine-based motif and BoNT/B with fused leucine-based motif, are administered concurrently or consecutively. While this invention has been described with respect to various specific examples and embodiments, it is to be understood that the invention is not limited thereto and that it can be variously practiced with the scope of the following claims.

What is claimed is:

1. A modified botulinum neurotoxin type E having increased biological half-life,
   wherein the modification is the addition of the leucine-based motif of SEQ ID NO: 1, and
   wherein the added leucine-based motif increases biological half-life of the modified botulinum toxin type E relative to an identical botulinum toxin type E without the added leucine-based motif.

2. The modified botulinum neurotoxin type E of claim 1, wherein the added leucine-based motif is SEQ ID NO: 11, SEQ ID NO: 13, SEQ ID NO: 16, or SEQ ID NO: 18.

3. A botulinum neurotoxin type E comprising a modification,
   wherein the modification is the addition of the leucine-based motif of SEQ ID NO: 1, and
   wherein the added leucine-based motif increases biological half-life of the botulinum toxin type E relative to an identical botulinum toxin type E without the added leucine-based motif.

4. The botulinum neurotoxin type E of claim 3, wherein the added leucine-based motif is SEQ ID NO: 11, SEQ ID NO: 13, SEQ ID NO: 16, or SEQ ID NO: 18.

* * * * *

UNITED STATES PATENT AND TRADEMARK OFFICE
CERTIFICATE OF CORRECTION

PATENT NO. : 7,671,177 B2 Page 1 of 1
APPLICATION NO. : 12/057642
DATED : March 2, 2010
INVENTOR(S) : Lance E. Steward et al.

It is certified that error appears in the above-identified patent and that said Letters Patent is hereby corrected as shown below:

On the Title page, in Item (73), Assignee, column 1, delete "(US)" and insert -- 92612 (US) --, therefor.

On page 2, under "Other Publications", in column 2, line 1, delete "Radinger" and insert -- Rudinger --, therefor.

In column 3, line 2, delete "hemaglutinin" and insert -- hemagglutinin --, therefor.

In column 3, line 3, delete "nonhemaglutinin" and insert -- nonhemagglutinin --, therefor.

In column 5, line 23, delete "norepinephine" and insert -- norepinephrine --, therefor.

In column 7, line 20, delete "leuine-based" and insert -- leucine-based --, therefor.

In column 7, line 44, delete "Acrch" and insert -- Arch. --, therefor.

In column 9, line 42, delete "SEQ ID NO: 7" and insert -- (SEQ ID NO: 7) --, therefor.

In column 11, line 42, delete "largyngeal" and insert -- laryngeal --, therefor.

In column 13, line 13, delete "Weigand" and insert -- Wiegand --, therefor.

In column 13, line 13, delete "Nauny-Schmiedeberg's" and insert -- Naunyn-Schmiedeberg's --, therefor.

In column 13, line 15, delete "Nauny-Schmiedeberg's" and insert -- Naunyn-Schmiedeberg's --, therefor.

In column 16, line 21, delete "catherization" and insert -- catheterization --, therefor.

Signed and Sealed this

Eighth Day of June, 2010

David J. Kappos
*Director of the United States Patent and Trademark Office*